United States Patent [19]

Ludvik

[11] Patent Number: 5,055,605
[45] Date of Patent: Oct. 8, 1991

[54] PREPARATION OF TRISUBSTITUTED BENZOIC ACID PRECURSORS

[75] Inventor: Charles N. Ludvik, Moraga, Calif.

[73] Assignee: Imperial Chemical Industries plc, London, England

[21] Appl. No.: 599,203

[22] Filed: Oct. 15, 1990

[51] Int. Cl.$^5$ ............................................. C07C 315/02
[52] U.S. Cl. .......................................... 560/11; 560/12; 562/429; 562/430; 568/28; 568/30; 568/31; 568/33
[58] Field of Search ................... 560/11, 12; 562/429, 562/430; 568/28, 30, 31, 33

[56] References Cited

U.S. PATENT DOCUMENTS 4,675,447 6/1987 Ludvik ................................. 568/28
4,780,127 10/1988 Michaely et al. ................. 71/103

Primary Examiner—José G. Dees
Assistant Examiner—Vera C. Clarke
Attorney, Agent, or Firm—Edwin H. Baker

[57] ABSTRACT

The process of the present invention relates to the preparation of precursor trisubstituted benzoic acid intermediates having the structural formula

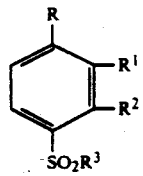

wherein
R is —COOR$^a$ wherein R$^a$ is C$_1$–C$_6$ alkyl; C$_1$–C$_4$ alkyl; formyl or C(O)R$^b$ wherein R$^b$ is C$_1$–C$_4$ alkyl;
R$^1$ is hydrogen, halogen, nitro, C$_1$–C$_2$ alkyl, C$_1$–C$_2$ alkoxy or trifluoromethyl;
R$^2$ is hydrogen, halogen, C$_1$–C$_4$ alkoxy, C$_1$–C$_4$ alkyl —OCH$_2$CH$_2$OCH$_3$, —OCH$_2$CH$_2$OC$_2$H$_5$ or a substituted methyl group and
R$^3$ is C$_1$–C$_4$ alkyl or C$_1$–C$_4$ haloalkyl.

10 Claims, No Drawings

PREPARATION OF TRISUBSTITUTED BENZOIC ACID PRECURSORS

BACKGROUND OF THE INVENTION

Certain 2-(2'3'4'trisubstituted benzoyl)-1,3-cyclohexanedione herbicides are described in U.S. Pat. No. 4,780,127, issued Oct. 25, 1988; U.S. Pat. No. 4,816,066, issued Mar. 28, 1989; and PCT International Publication No. WO 90/05712, published May 31, 1990, and entitled Certain 2-(2',3',4'-trisubstituted benzoyl)-1,3-cyclohexanediones, with William J. Michaely, inventor and all incorporated herein by reference.

The above-described herbicidal compounds can have the following structural formula

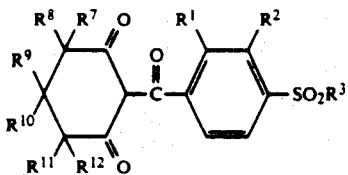

wherein $R^1$ is hydrogen, halogen, nitro, $C_1$-$C_2$ alkyl, $C_1$-$C_2$ alkoxy or trifluoromethyl; $R^7$ through $R^{12}$ are hydrogen or $C_1$-$C_4$ alkyl or. $R^7$, $R^8$, $R^{11}$ and $R^{12}$ are methyl and $R^9$ and $R^{10}$ together is carbonyl; $R^2$ is hydrogen, halogen, $C_1$-$C_4$ alkoxy, $C_1$-$C_4$ alkyl —OCH$_2$CH$_2$OCH$_3$, —OCH$_2$CH$_2$OC$_2$H$_5$, or a substituted alkyl preferably $C_1$-$C_4$ alkoxy, $C_1$-$C_4$ alkyl, $C_1$-$C_4$ haloalkyl, —CH$_2$CH$_2$OCH$_3$, —CH$_2$CH$_2$OC$_5$, or $C_1$-$C_2$ alkoxy methylene; and $R^3$ is $C_1$-$C_4$ alkyl or $C_1$-$C_4$ haloalkyl.

These herbicides can be prepared by reacting a dione of the structural formula

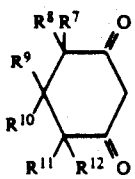

wherein $R^7$ through $R^{12}$ are as defined with a mole of a trisubstituted benzoyl chloride compound of the structural formula

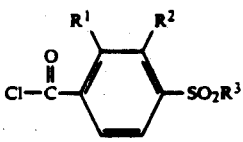

wherein $R^1$, $R^2$ and $R^3$ are as defined above.

The process of the present invention relates to the preparation of precursor trisubstituted benzoic acid intermediates that are easily converted to the above described trisubstituted benzoyl chloride compounds.

U.S. Pat. No. 4,780,127 teaches the preparation of 2,3 disubstituted-4-(alkylsulfonyl) benzoic acid by the oxidation of the corresponding 2,3-disubstituted-4-(alkylthio) benzoic acid with an oxidizing agent such as sodium hypochlorite or m-chloroperbenzoic acid in a solvent such as methylene chloride. Hydrogen peroxide is not specifically recited as an oxidizing agent.

However, hydrogen peroxide ($H_2O_2$) is a well known oxidizing agent for converting aliphatic or aromatic sulfides to sulfoxides. Customarily, the hydrogen peroxide is used with an equal mole amount of formic acid which reacts with the hydrogen peroxide to form the more active performic acid oxidizing agent. However, the oxidation reaction yields formic acid which is an undesireable reaction product for the process of this invention.

Hydrogen peroxide, for safety reasons, normally is diluted with water to concentrations of about 30 or 50 percent by weight when used as an oxidizing agent. When these 30 or 50 percent hydrogen peroxide solutions are used as an oxidizing agent for sulfides the reaction is very slow at normal temperatures (20° C.-100° C.).

When an aqueous hydrogen peroxide solution at high concentrations (above 90 percent by weight) is used as the oxidizing agent for converting sulfides to sulfones, the oxidation is initially successful but quickly becomes inefficient.

The reason for this is that the normal reaction mechanism is that one mole of hydrogen peroxide first will oxidize the sulfide reactant to the corresponding sulfoxide with the creation of one mole of water according to the following equation:

$$R'-S-R''+H_2O_2 \rightarrow R'-S(O)-R''=H_2O$$

It can be seen that as the oxidation reaction proceeds, the concentration of the aqueous hydrogen peroxide solution is increasingly diluted with additional water that is created by the reaction and increasingly the hydrogen peroxide becomes less effective as an oxidizing agents as the concentration of the aqueous solution of hydrogen peroxide becomes less and less.

SUMMARY OF THE INVENTION

The present invention relates to an improved process for the preparation of the hereinafter-described sulfone herbicide intermediates by a reaction step comprising the oxidation of the hereinafter described corresponding sulfide herbicide intermediate using an aqueous solution of hydrogen peroxide. Basically, the improvement comprises maintaining during the reacting step or substantially throughout the entire time of the oxidation the concentration of the aqueous solution of hydrogen peroxide at a high concentration (above 70 percent by weight based upon the combined weight of the hydrogen peroxide and water in the reaction mixture).

A high concentration of the hydrogen peroxide is maintained throughout the reaction time period by the constant or periodic removal of water from the reaction mixture at such times or at such rates so as to not allow the concentration of the hydrogen peroxide to fall below 70 percent by weight.

Water is removed from the reaction mixture of (1) sulfide reactant (2) a solvent that is not misicible with water (3) hydrogen peroxide and (4) water, preferably by the azeotropic distillation of water and solvent. Preferably the distillation is carried out at a temperature below about 100° C., more preferably below about 90° C.

The distillate of water and solvent can be separated and solvent returned to the reaction vessel by conventional techniques if necessary to maintain sufficient solvent in the reaction vessel.

DETAILED DESCRIPTION OF THE INVENTION

This invention relates to a process for preparing compounds having the structural formula

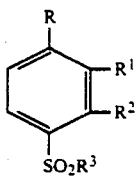

wherein

R is (1)—COOR$^a$ wherein R$^a$ is C$_1$-C$_6$ alkyl, preferably C$_1$-C$_4$ alkyl, more preferably ethyl, n-propyl, or n-butyl; (2) C$_1$-C$_4$ alkyl, preferably C$_1$-C$_2$ alkyl, more preferably methyl; (3) formyl or (4)—C(O) R$^b$ wherein R$^b$ is C$_1$-C$_4$ alkyl, preferably methyl, most preferably R is —COOR$^a$ wherein R$^a$ is ethyl or n-propyl, R$^1$ is hydrogen; halogen, preferably chlorine or bromine, more preferably chlorine; nitro; C$_1$-C$_2$ alkyl, preferably methyl; C$_1$-C$_2$ alkoxy, preferably methoxy; or trifluoromethyl, most preferably R$^1$ is chlorine or nitro, R$^2$ is hydrogen; halogen, preferably chlorine; C$_1$-C$_4$ alkoxy, preferably methoxy or ethoxy; —OCH$_2$OC$_2$H$_5$; —OCH$_2$OCH$_3$; C$_1$-C$_4$ preferably methyl; a substituted C$_1$-C$_4$ alkyl group, preferably C$_1$-C$_4$ haloalkyl, more preferably chloromethyl or trifluoromethyl; —CH$_2$OCH$_3$; —CH$_2$OC$_2$H$_5$; or —C(O)OR$^c$ wherein R$^c$ is C$_1$-C$_4$ alkyl, and R$^3$ is C$_1$-C$_4$ alkyl, preferably methyl or ethyl or C$_1$-C$_4$ haloalkyl, preferably chloromethyl by a step of reacting a compound having the structural formula

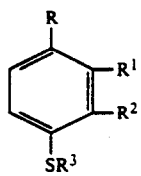

wherein R, R$^1$, R$^2$ and R$^3$ are as defined with hydrogen peroxide under conditions defined herein.

In the above-described process of this invention the reacting step must be (1) run in a solvent that is immiscible with water and which has an azeotroping temperature with water of less than 100° C.; preferably less than 90° C., and (2) carried out the reacting step while the concentration of the hydrogen peroxide is maintained at a concentration of above 70 percent by weight (preferably 90 percent by weight) based upon the weight of the hydrogen peroxide and any water present in the reaction mixture.

Examples of such solvents that have an azeotropic temperature with water of less than 100° C. and which are useful in the practice of this invention are as follows:

| Solvent | b.p. of azeotrope | b.p. of solvent | % solvent in azeotrope |
|---|---|---|---|
| toluene | 85° C. | 111° C. | 80% |
| o-xylene | 94° C. | 144° C. | 50% |
| m-xylene | 93° C. | 139° C. | 55% |
| benzene | 69° C. | 80° C. | 91% |
| cyclohexane | 69° C. | 81° C. | 91% |
| hexane | 62° C. | 69° C. | 94% |
| heptane | 79° C. | 98° C. | 87% |
| octane | 90° C. | 126° C. | 75% |
| 1-butanol | 93° C. | 118° C. | 58% |
| ethylacetate | 70° C. | 88° C. | 92% |
| butylacetate | 90° C. | 116° C. | 71% |
| isobutylacetate | 87° C. | 116° C. | 83% |
| chlorobenzene | 90° C. | 112° C. | 72% |
| carbon tetrachloride | 66° C. | 77° C. | 96% |
| EDC (ethylene dichloride) | 72° C. | 83° C. | 92% |
| trichloroethane | 65° C. | 74° C. | 92% |

Toluene, xylene and ethylene dichloride are the preferred solvents.

The process of this invention can be better understood by considering the preceeding discussion of the process of this invention and the following specific examples.

EXAMPLE I

This example teaches the preparation of the n-propyl ester of 2-nitro-4-methylsulfonyl benzoic acid by the oxidation of the n-propyl ester of 2-nitro-4-methylthiobenzoic acid by the process of this invention.

Two hundred fifty grams of a 25% toluene solution of the n-propyl ester of 2-nitro-4-methylthiobenzoic acid (62.5 g, 0.25 mole) were added to a multi-necked round bottom flask equipped with a condenser, mechanical stirrer, thermometer, dropping funnel and Dean-Stark trap. The stirred solution was heated to 95° C. One hundred grams of a 30% aqueous solution of hydrogen peroxide (30 g, 0.88 mole) were added slowly to the toluene solution through a dropping funnel over about 3 to 4 hours to control foaming, to remove water by the azeotropic distillation of toluene and water, and to start the oxidation reaction. The temperature was maintained at 90° C.-100° C. during the addition. Water was removed from the reaction mixture by azeotropic distillation and drained periodically from the Dean-Stark trap where it had collected. The reaction was monitored by a Hewlitt-Packard Mode 1090 high performance liquid chromatograph with ultraviolet detector and the oxidation reaction was determined to be complete about 1 hour after all the hydrogen peroxide was added.

The prepared n-propyl ester of 2-nitro-4-methylsulfonyl benzoic acid was not isolated but instead it was hydrolyzed to 2-nitro-4-methylsulfonyl benzoic acid for recovery. To the same reaction flask was charged 290 g water and 34 g 50% sodium hydroxide solution (17 g, 0.42 mole). The mixture was heated to 25° C.-30° C. and held for six hours to hydrolyze the ester. The aqueous phase was cooled to 5° C. -10° C. and 80 g of 25% sulfuric acid (20 g, 0.2 mole) was slowly added with agitation. The product was filtered and dried to give 43.0 g of solids. The purity of the 2-nitro-4-methysulfonyl benzoic acid was 92.7% by weight when compared to an anaylitical reference standard. The yield was about 66% from the n-propyl ester of 2-nitro-4-methylthiobenzoic acid to the 2-nitro-4-methylsulfonylbenzoic acid.

EXAMPLE II

This example teaches the preparation of the n-propyl ester of 2-chloro-4-methylsulfonyl benzoic acid by the oxidation of the n-propyl ester of 2-chloro-4-methylthiobenzoic acid by the process of this invention.

One hundred forty-one grams of a 43.5% toluene solution of the n-propyl ester of 2-chloro-4-methylthiobenzoate (61.1 grams, 0.25 mole) were added to a multi-necked round bottom flask equipped with a condenser, mechanical stirrer, thermometer, dropping funnel and Dean-Stark trap. The stirred solution was heated to 95° C. Eighty-six grams of a 30% aqueous solution of hydrogen peroxide (25.8 g, 0.76 mole) were added slowly to the toluene solution through a dropping funnel over about 2 to 3 hours to control foaming, to remove water by azeotropic distillation, and to start the oxidation reaction. The temperature was maintained at 90° C.-100° C. during the addition. Water was removed from the reaction mixture by azeotropic distillation and drained periodically from the Dean-Stark trap where it had collected. The reaction was monitored by a Hewlitt-Packard Mode 1090 high performance liquid chromatograph and the oxidation reaction was determined to be complete about 1 hour after completion of the addition of the hydrogen peroxide. The concentration of the hydrogen peroxide aqueous solution was increased to over 70 percent by weight a few minutes after the start of the addition and was maintained at this concentration throughout the reaction time period.

The prepared n-propyl ester of 2-chloro-4-methylsulfonyl benzoate was not isolated but instead hydrolyzed to 2-chloro-4-methylsulfonyl benzoic acid for recovery. To the reaction flask was charged 230 g water and 28 g 50% sodium hydroxide solution (14 g, 0.35 mole). The mixture was heated to 50° C. and held for two hours to hydrolyze the ester. The aqueous phase was cooled to 5° C.-10° C. and 40 g of 37% hydrochloric acid (14.8 g, 0.4 mole) was slowly added with agitation. The product was filtered and dried to give 51.5 g of solids. The purity of the 2-chloro-4-methylsulfonyl benzoic acid was 98.3 percent by weight when compared to an analytical reference standard. The yield was about 90% from the n-propyl ester of 2-chloro-4-methyl-thiobenzoic acid to the 2-chloro-4-methylsulfonylbenzoic acid.

What is claimed is:

1. An improved process for the preparation of a compound having the structural formula

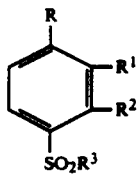

wherein
R is $-COOR^a$ wherein $R^a$ is $C_1-C_6$ alkyl; $C_1-C_4$ alkyl; formyl or $C(O)R^b$ wherein $R^b$ is $C_1-C_4$ alkyl;
$R^1$ is hydrogen, halogen, nitro, $C_1-C_2$ alkyl, $C_1-C_2$ alkoxy or trifluoromethyl;
$R^2$ is hydrogen, halogen, $C_1-C_4$ alkoxy, $C_1-C_4$ alkyl, $-OCH_2CH_2OCH_3$, $-OCH_2CH_2OC_2H_5$ or a substituted methyl group and
$R^3$ is $C_1-C_4$ alkyl or $C_1-C_4$ haloalkyl
comprising a step of reacting a compound having the structural formula

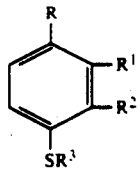

wherein R, $R^1$, $R^2$ and $R^3$ are as defined with hydrogen peroxide and water wherein the improvement comprises a) running the reacting step in a solvent that is immisicible with water and has an azeotroping temperature with the water of less than 100° C., and b) maintaining during the reacting step the concentration of the hydrogen peroxide at above 70 percent by weight based upon the combined weight of the hydrogen peroxide and water in the reaction mixture.

2. The process of claim 1 wherein R is $-COOR^a$ wherein $R^a$ is $C_1-C_6$ alkyl, $R^1$ is chlorine, bromine, nitro, trifluoromethyl, or methyl; $R^2$ is hydrogen, chlorine, $C_1-C_2$ alkoxy, $-OCH_2CH_2OCH_3$, $-OCH_2CH_2OC_2H_5$, or $-CH_2OCH_3$; $R^3$ is $C_1-C_2$ alkyl and the solvent is toluene.

3. The process of claim 2 wherein $R^a$ is n-propyl, $R^1$ is chlorine, $R^2$ is hydrogen and $R^3$ is methyl.

4. The process of claim 2 wherein $R^a$ is n-propyl, $R^1$ is nitro, $R^2$ is hydrogen, $R^3$ is methyl.

5. The process of claim 2 wherein $R^a$ is n-propyl, $R^1$ is chlorine, $R^2$ is ethoxy and $R^3$ is ethyl.

6. The process of claim 1 wherein the solvent is toluene, xylene or ethylene dichloride.

7. The process of claim 1 wherein the solvent is toluene and concentration of the hydrogen peroxide is maintained at above 90 percent by weight based upon the combined weight of the hydrogen peroxide and water in the reaction mixture.

8. The process of claim 2 wherein the solvent is toluene and concentration of the hydrogen peroxide is maintained at above 90 percent by weight based upon the combined weight of the hydrogen peroxide and water in the reaction mixture.

9. An improved process for the preparation of a compound having the structural formula

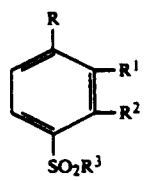

wherein
R is $-COOR^a$ wherein $R^a$ is $C_1-C_6$ alkyl; $C_1-C_4$ alkyl; formyl or $C(O)R^b$ wherein $R^b$ is $C_1-C_4$ alkyl;
$R^1$ is hydrogen, halogen, nitro, $C_1-C_2$ alkyl $C_1-C_2$ alkoxy or trifluoromethyl;
$R^2$ is hydrogen, halogen, $C_1-C_4$ alkoxy, $C_1-C_4$ alkyl $-OCH_2CH_2OCH_3$, $-OCH_2CH_2OC_2H_5$ or a substituted methyl group and
$R^3$ is $C_2-C_4$ alkyl or $C_1-C_4$ haloalkyl
comprising a step of reacting a compound having the structural formula

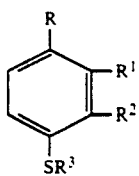

wherein R, R[1], R[2] and R[3] are as defined with hydrogen peroxide and water wherein the improvement comprises a) running the reacting step in a solvent that is immiscible with water and has an azeotroping temperature with the water of less than 100° C., and b) maintaining during the reacting step the concentration of the hydrogen peroxide at above 70 percent by weight based upon the combined weight of the hydrogen peroxide and water in the reaction mixture by the azeotropic distillation of water and solvent.

10. The process of claim 9 wherein the solvent is toluene, xylene or ethylene dichloride and the azeotropic distillation is carried out at a temperature below about 100° C.

* * * * *